United States Patent
Commereuc et al.

(10) Patent No.: US 6,846,465 B2
(45) Date of Patent: Jan. 25, 2005

(54) VIBRATORY HELICOIDAL CONVEYOR FOR TREATMENT OF METATHESIS CATALYSTS FOR OLEFINS

(75) Inventors: Dominique Commereuc, Meudon (FR); Hélène Olivier, Rueil Malmaison (FR); Lucien Saussine, Croissy sur Seine (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 824 days.

(21) Appl. No.: 09/837,379

(22) Filed: Apr. 19, 2001

(65) Prior Publication Data

US 2001/0014299 A1 Aug. 16, 2001

Related U.S. Application Data

(62) Division of application No. 09/339,109, filed on Jun. 24, 1999, now Pat. No. 6,265,501.

(30) Foreign Application Priority Data

Jun. 24, 1998 (FR) .............................. 98 07984

(51) Int. Cl.[7] .......................... B01D 50/00; B01D 53/34
(52) U.S. Cl. ...................... 422/178; 422/177
(58) Field of Search ................................. 422/178, 177, 422/168

(56) References Cited

U.S. PATENT DOCUMENTS

| | | | | |
|---|---|---|---|---|
| 2,894,824 A | * | 7/1959 | Lanning | 422/137 |
| 3,460,821 A | * | 8/1969 | Salat et al. | 266/204 |
| 4,035,151 A | * | 7/1977 | Czemy et al. | 422/232 |
| 4,575,575 A | * | 3/1986 | Drake et al. | 585/646 |
| 5,508,243 A | * | 4/1996 | Mitzkat et al. | 502/5 |
| 5,592,748 A | * | 1/1997 | Mitzkat et al. | 34/61 |

FOREIGN PATENT DOCUMENTS

| | | |
|---|---|---|
| EP | 0 612 561 | 8/1994 |
| FR | 2 258 895 | 8/1975 |
| FR | 2 608 595 | 6/1988 |
| FR | 2 634 187 | 1/1990 |

* cited by examiner

*Primary Examiner*—M. Alexandra Elve
(74) *Attorney, Agent, or Firm*—Millen, White, Zelano & Branigan, P.C.

(57) ABSTRACT

A vibratory helidcoidal lifting device (12) suitable for regenerating metathesis catalysts for olefins, comprises a combustion zone (14) and a calcination zone (15), as well as a preheating zone, a zone for stripping hydrocarbons and a zone for cooling the catalyst, but no zone for introducing a gas containing a halogenated compound.

1 Claim, 2 Drawing Sheets

VIBRATORY HELICOIDAL CONVEYOR FOR TREATMENT OF METATHESIS CATALYSTS FOR OLEFINS

CROSS REFERENCE TO RELATED APPLICATION

Figure 1:
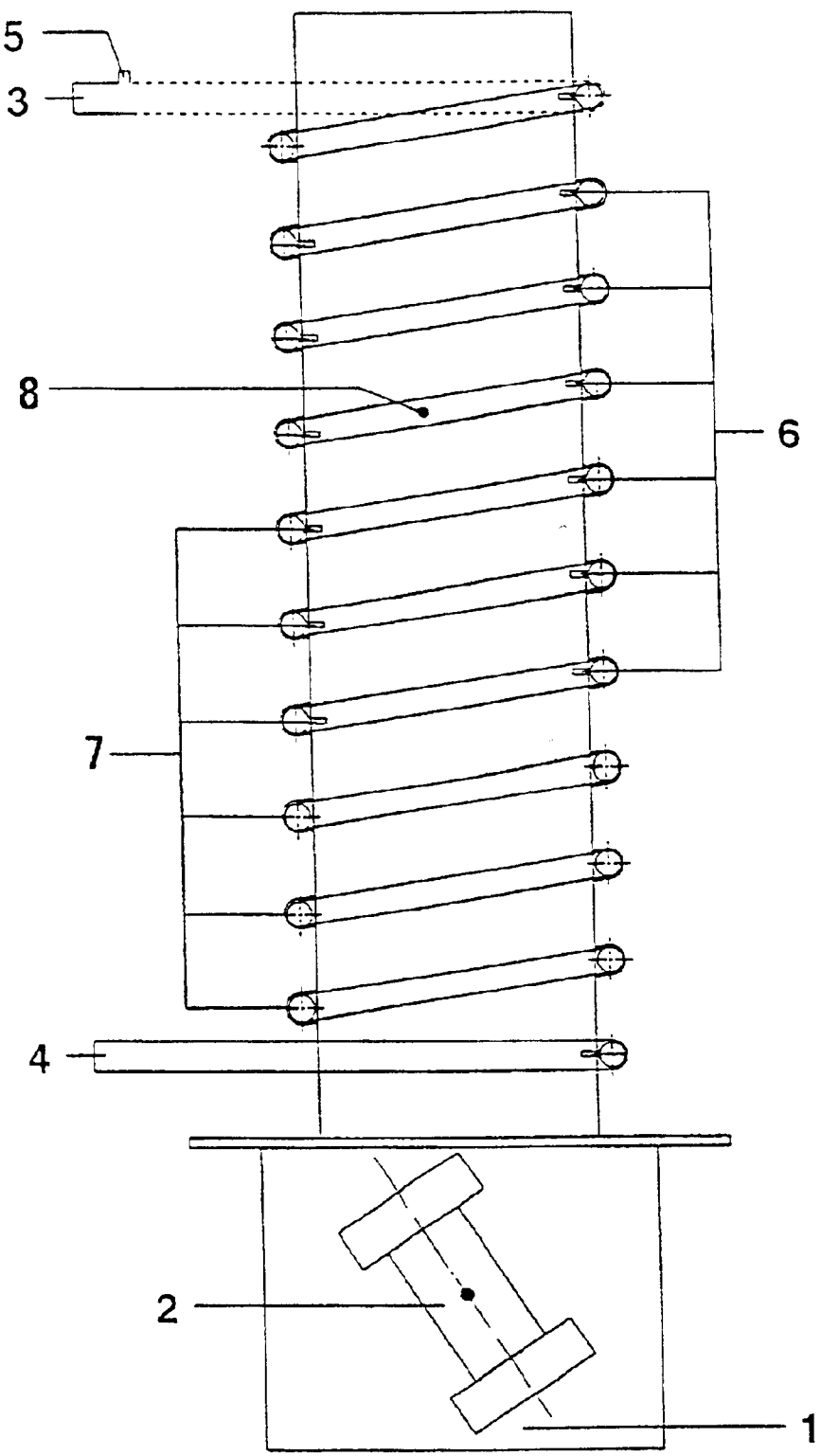

This application may be related to Assignee's concurrently filed application Ser. No. 09/339,109, entitled "Regeneration Of Catalysts For Reforming Or Isomerizing Or Dehydrogenating Paraffins By Shifting Into A Descending Mode On A Vibratory Helicoidal Conveyor", based on French application 98/07.985 filed Jun. 24, 1998, inventor being Olivier Clause.

This invention relates to a process for treatment of metathesis catalysts (-regeneration, activation, reactivation).

Patent FR 2.608.595 of the French Petroleum Institute describes a process for continuous regeneration of metathesis catalysts with a rhenium base. This patent describes a process in which the catalyst flows out under the action of gravity from top to bottom of a column that is called a regenerator by successively passing through zones where stages of stripping, combustion, calcination and cooling are carried out. This requires conveying the catalyst from the bottom of the metathesis reactor through which the feedstock passes toward the top of the regenerator, then in bringing the catalyst back from the bottom of the regenerator toward the top of the reactor. This conveying of catalysts that is carried out by, for example, liquid or gaseous lifts, is able to gradually deteriorate the catalyst, for example by generating fines and powders or by breaking catalyst particles.

The applicant now sought to improve the regeneration of the metathesis catalyst.

This invention relates to a process for treatment of metathesis catalysts for olefins, polyolefins or acetylenic compounds that consists in conveying the catalyst particles into at least one vibratory helicoidal conveyor that contains at least one vibratory helicoidal coil, in subjecting them over at least a portion of their path and preferably over a major portion of their path to a temperature profile, and in bringing them into contact with at least one fluid over at least a portion of their path.

The transit of the catalyst particles in the vibratory helicoidal conveyor can be carried out according to an ascending mode or descending mode.

The treatment of said catalyst can be carried out continuously or by batch, preferably it is carried out continuously.

In this description, the means that comprises at least one vibratory helicoidal coil in which the catalyst particles transit is called "vibratory helicoidal conveyor," and when the process operates in ascending mode, said vibratory helicoidal conveyor is called "vibratory helicoidal lifting device"; in contrast, the term "olefins" more generally covers olefins, polyolefins and acetylenic compounds.

The metathesis process of the olefins consists in causing one or more olefins to react on themselves or among themselves, which gives rise to a redistribution of the alkylidene groups of the olefins of the feedstock and thus produces new olefins. This reaction offers great practical significance, for example for the rebalancing between them of the light olefins that are obtained from the steam cracking, such as ethylene, propylene and butenes. These olefins are used below for the production of polymers and/or copolymers.

The process for metathesis of olefins uses catalysts that are integral with metal or metal oxide bases, such as molybdenum, tungsten, rhenium, titanium, niobium, tantalum, ruthenium, alone or in a mixture, supported on refractory oxides such as alumina, silica, silica-alumina, zeolites, titanium oxide, zirconia, magnesia, thorine, tin oxide, used alone or mixed. These catalysts can also be doped by the addition of components that increase or reduce their acidity, for example salts of fluoride, chloride, sulfate or phosphate anions, salts of alkaline or alkaline-earth metals, such as potassium, cesium, barium, salts or complexes of boron, aluminum or gallium, for example boron trifluoride, aluminum trichloride or aluminum complexes that comprise alkyl, alkoxy or aryloxy groups.

Over time, these catalysts are deactivated. In the case of catalysts that operate at relatively high temperature (200 to 400° C.), as is the case of catalysts with a molybdenum or tungsten base, the deactivation is attributed to the gradual deposition of complex-structure polyaromatic hydrocarbons that bear the common name of coke. In the case of catalysts that operate at low temperature (less than 150° C.), as is the case of catalysts with a rhenium base, the deactivation is attributed at least in part to the accumulation of impurities that are contained in the feedstocks that are to be treated and to the formation of polymers that clog the porous network of the catalyst.

The deposition of coke, polymers, or more generally impurities makes it necessary to regenerate the catalyst at the end of an operating cycle of from one or several days to several weeks. In the continuous regeneration units of the catalyst, it is not necessary to stop the units to initiate the regeneration of the catalyst. The catalyst is conveyed from the reactor (or reactors) to a regenerator that carries out the rejuvenation of the catalyst by a suitable process, and the conveying is carried out by means of a mechanical or pneumatic nature, then the regenerated catalyst is brought back toward the reactor (or reactors) by the same means.

To implement the process according to the invention, the regenerator can also be used off-site, for example the catalyst can be conveyed to a company that is specialized in the treatment of catalysts where it will be regenerated.

The regeneration of the metathesis catalysts can comprise a single stage, and this stage is then combustion that is provided in an oxidizing medium. The purpose of this stage is the elimination of the coke, accumulated impurities and polymers that are deposited on the catalyst. This stage generally consists in passing over said catalyst a gas that contains between 0.1 and 5% of molecular oxygen at a temperature of between 350° C. and 800° C., whereby the duration of this stage is longer than 10 minutes and preferably between 1 and 12 hours. Most often, the metathesis catalyst is dried before being used in the reaction zone.

In a preferred manner, the regeneration of the metathesis catalysts comprises a combustion stage that is provided following a calcination stage that is intended to improve the attachment of the active phase, to dry the catalyst and adjust its acidity to the value that is required for optimum catalytic performance levels.

The combustion stage that is provided consists in treating the catalyst between 350° C. and 800° C. by a gas that contains 0.1 to 5% of molecular oxygen for a period that is more than 10 minutes and preferably between 1 and 12 hours. The calcination stage consists in treating the catalyst for a duration that is longer than 10 minutes and preferably between 1 and 12 hours, at a temperature that is between 400° C. and 800° C.—whereby this temperature is generally higher than the temperature of the combustion zone that is provided—by a gas that contains 5 to 40%, and preferably 15 to 25% molecular oxygen, and this gas can be, for example, air.

These two stages that are carried out successively—in separate combustion and calcination zones that are arranged one on top of the other in the vibratory helicoidal conveyor in the direction of flow of the catalyst—or simultaneously—in combined combustion and calcination zones—can also be preceded by a stage of stripping hydrocarbons that are trapped in the pores of the catalyst under a stream of inert gas, for example under nitrogen, and can be followed by a stage of cooling of the catalyst under a dry gas, whereby this gas can be air or nitrogen.

These stages are, for example, used in the meta-4 process of the French Petroleum Institute (French Patent FR 2,608, 595), which is a continuous regeneration process of metathesis catalysts with a rhenium base.

The process according to this invention is used with a helicoidal conveyor that is driven in vibrations whose force resultant that is applied to the catalyst particles is calculated to make possible either the rise or the fall of these catalyst particles.

The helicoidal conveyor—or optionally the helicoidal conveyors—comprises at least one coil and is wound around a hollow drum in which is placed a system that is intended to produce the vibrations that are necessary for the catalyst particles to rise or fall. The vibrations can be produced by at least one system that is placed at any suitable level, for example at the bottom or at the top of the drum or else positioned around the helix. Among the systems that it is possible to use are the following systems: unbalanced motors, electromagnetic vibrations (excited by a variable cycle, with creation of pulses) and unbalanced excitations. The vibrations preferably are produced by a table that is used as a support for the central drum and is actuated by two unbalanced motors.

The acceleration that is imparted to the particles which are in motion in the coils comprises a vertical component and a horizontal component. According to the orientation of the horizontal component, the particles will rise or fall, the displacement speed of the particles is correlated with the horizontal component of the vibration.

The vibrations that are imparted to the drum-coil unit comprise the non-dimensional acceleration constant, ratio of the vertical component of acceleration to the acceleration of the weight, between 0 and 4, preferably between 1.2 and 3.5, and even more preferably between 1 and 3, whereby the rate of advance of the particles is generally between 0.02 and 0.5 m/s. The mass rate of particles per hour is generally between 1 kg/h and 50 tons/h, preferably between 5 kg/h and 10 tons/h.

In the case of the preferred use according to the invention, the vibrations are produced by a table that is used as a support for the central drum and is actuated by two unbalanced motors. In this case, the solid particles that are conveyed inside the vibratory helicoidal conveyor advance at a speed that is proportional to the non-dimensional acceleration constant, for a given motor inclination and angle of climb. The non-dimensional acceleration constant depends on the spacing of the imbalances and their speed of rotation for the given system. For example, for a variation of said constant between 1.2 and 3.5, the rate of advance of the particles is typically between 0.1 and 0.3 m/s. Said speed thus can be easily adjusted by acting on the spacing of the imbalances, the inclination of the motors or the speed of rotation of the motors. In regard to the hourly volumetric flow rate of the particles, it depends on the non-dimensional vibration constant, but also the diameter of the tube that forms the coil. The power of the motors and the space requirement within the tube are limiting factors. In contrast, the inclination of the motors generally should not exceed 350 to advance the solid particles effectively in the tube without producing excessive vibrations.

The turns of the helix that the conveyor describes can be contiguous or non-contiguous. The turns generally have a developed length of between 0 and 500 m, and the height of the helix is generally between 0 and 20 m. The angle of climb of the turn that measures the inclination of the turn relative to the horizontal line is between 10° and preferably between 1 and 5° and even more preferably between 1 and 4°.

The embodiments of the process according to this invention in which the conveying of the catalyst that is to be regenerated is carried out according to the ascending mode makes it possible to avoid, at least in part, the use of a process of conveying the catalyst toward the top of the regenerator and from the bottom of the regenerator. The device for use of the process is actually a regenerator that is fed by the catalyst in its low portion, whereby the regenerated catalyst exits at the top of the regenerator. Therefore, at the same time that the regeneration of the catalyst is initiated, it is at least partially raised simultaneously toward the top of the metathesis reaction zone.

The helicoidal lifting devices that are generally used are those that are described in Application FR 2634187; they comprise at least one coil. Their height is often less than that of the reactors. Also, even if the use of such helicoidal lifting devices makes possible the rising of the catalyst particles toward the top of the reaction zone, this rise is often only partial. The use of "lifts" is therefore often necessary for conveying the catalyst particles to the input of the reaction zone.

The device can be used in a circulating bed metathesis process or during off-site regeneration of the metathesis catalyst. The catalyst particles that rise within the coil are subjected to a temperature profile over a portion of their path. This temperature profile can be obtained by indirect contact with a coolant that bathes the spans of the helix, as is described in French Patent Application 2 634 187. In this patent application, the turns of the helicoidal ramp are connected to one another by two helicoidal strips, which are attached to a ramp on two opposing sides of the latter to form a helicoidal channel, and between the turns of the helicoidal ramp and in this channel, a coolant can circulate.

More generally, as is described in French Patent 943,865, the entire drum-conveyor device can be placed in a container where the products that are conveyed will be subjected to heat treatment, for example, a heat-insulated container in which a coolant that bathes the spans of the helix circulates. The same patent application teaches that the coolant can pass through the coil itself. This gas can circulate in co-current or counter-current. The heating of the coil can also be achieved by the Joule effect, by directly heating the metal mass of the tube, as is described in European Patent Application EP-A-612561.

According to a preferred embodiment of this invention, the catalyst particles rise in a vibratory helicoidal lifting device that comprises at least one vibratory helicoidal coil and in which are arranged at least one combustion zone and optionally at least one calcination zone. According to said process, the particles are also subjected to a temperature profile over at least a portion of their path, a path during which they are brought into contact with at least one fluid. The process according to the invention then relates to a treatment in the group that is formed by the regenerations, the activations, the reactivations of catalysts, and it comprises at least one combustion stage that is produced in at least one combustion zone and optionally at least one calcination stage that is produced in at least one calcination zone.

By rising in the helicoidal lifting device, the catalyst successively passes through a zone for combustion of coke, impurities and polymers where a flow of air or oxygen that is suitably diluted by an inert gas, for example by nitrogen, is introduced in stages at several successive coils to limit the oxygen concentration and to not risk degrading the catalyst by local overheating, and optionally a calcination zone where the catalyst is flushed by a stream of dry air that contains less than 200 ppm of water. It is possible to combine the combustion and calcination zones in a single zone.

Advantageously, the combustion stage is preceded by a stage for stripping hydrocarbons that are trapped in the pores of the catalyst under a stream of inert gas, for example under nitrogen, and a stage in which the catalyst is preheated such that its temperature reaches a level where the subsequent combustion of the coke is carried out under optimum conditions. The calcination stage is generally followed by a cooling stage of the catalyst under air or preferably under dry nitrogen that contains less than 50 ppm of water.

It is also possible to modulate the injections of air or oxygen into the combustion stage by introducing, for example, increasing quantities of air from bottom to top of the helicoidal lifting device. The temperatures of the gases at the inlet of the combustion zone can be between 300 and 800° C., and preferably between 450 and 550° C. It is also possible to withdraw a portion of the combustion gases using purges that are placed in one or more locations of the lifting device.

The helix, or helices if there are several of them, comprises at least one turn and is wound around a hollow drum in which is placed a system that is intended to produce vibrations, for example an unbalanced motor as described in French Patent 943,865. The turns can be contiguous or non-contiguous. The gases or fluids that are intended for the regeneration of the metathesis catalysts can be introduced by one or more hoses such that said gases or fluids circulate in co-current or countercurrent in one or more spans of the coil. The pressure within the coil can be between 0.1 and 20 bar, preferably between 1 and 7 bar. The gases or fluids can be introduced into the coil laterally, above or below the coil, by passing through a fine-mesh lattice or through any suitable device that is intended to prevent catalyst particles from penetrating into the gas intake hoses. The same holds true for the hose or hoses for drawing off gases.

The invention also relates to a metathesis process in which the catalyst circulates from top to bottom in a reaction zone in which the metathesis is produced, is drawn off at the bottom of the reaction zone, is sent into a vibratory helicoidal conveyor in which it is treated according to the treatment process of this invention, then is drawn off from said vibratory helicoidal conveyor to be sent to the top of the reaction zone. A vibratory helicoidal conveyor that operates in ascending mode will preferably be selected.

It is equally possible to use a vibratory helicoidal conveyor that operates in descending mode particularly when the metathesis process is carried out in a reaction zone in which the catalyst circulates from bottom to top.

This invention also relates to an installation for use of the treatment process according to this invention that comprises at least one vibratory helicoidal conveyor that comprises at least one coil that is placed on a vibrating table, at least one hose for introducing catalyst and at least one catalyst discharge hose. This installation also contains at least one combustion zone in which is placed at least one coil of the vibratory helicoidal conveyor that comprises at least one hose for introducing gases and at least one gas discharge hose. Said installation preferably also comprises at least one calcination zone in which is placed at least one coil of the vibratory helicoidal conveyor that comprises at least one hose for introducing gases and at least one gas discharge hose. Said installation, however, a does not comprise a zone in which a gas that contains a halogenated compound is introduced.

FIG. 1 describes a simple embodiment of the process according to the invention that operates in descending mode. This embodiment actually comprises a single so-called combustion zone in which the coke and the impurities that are deposited on the catalyst are eliminated with a combustion gas.

Helicoidal conveyor (8) is placed on a vibrating table (1), and two unbalanced motors (2) generate the vibrations that are necessary for the catalyst to fall. The solid catalyst particles enter via hose (3) and exit via hose (4). A gas is introduced via hose (5) at the top of the device and via six hoses (6) at several levels of the helicoidal conveyor. Said gas passes through the helicoidal conveyor at co-current with the catalyst and then exits from the device via six hoses (7).

Figure 2:
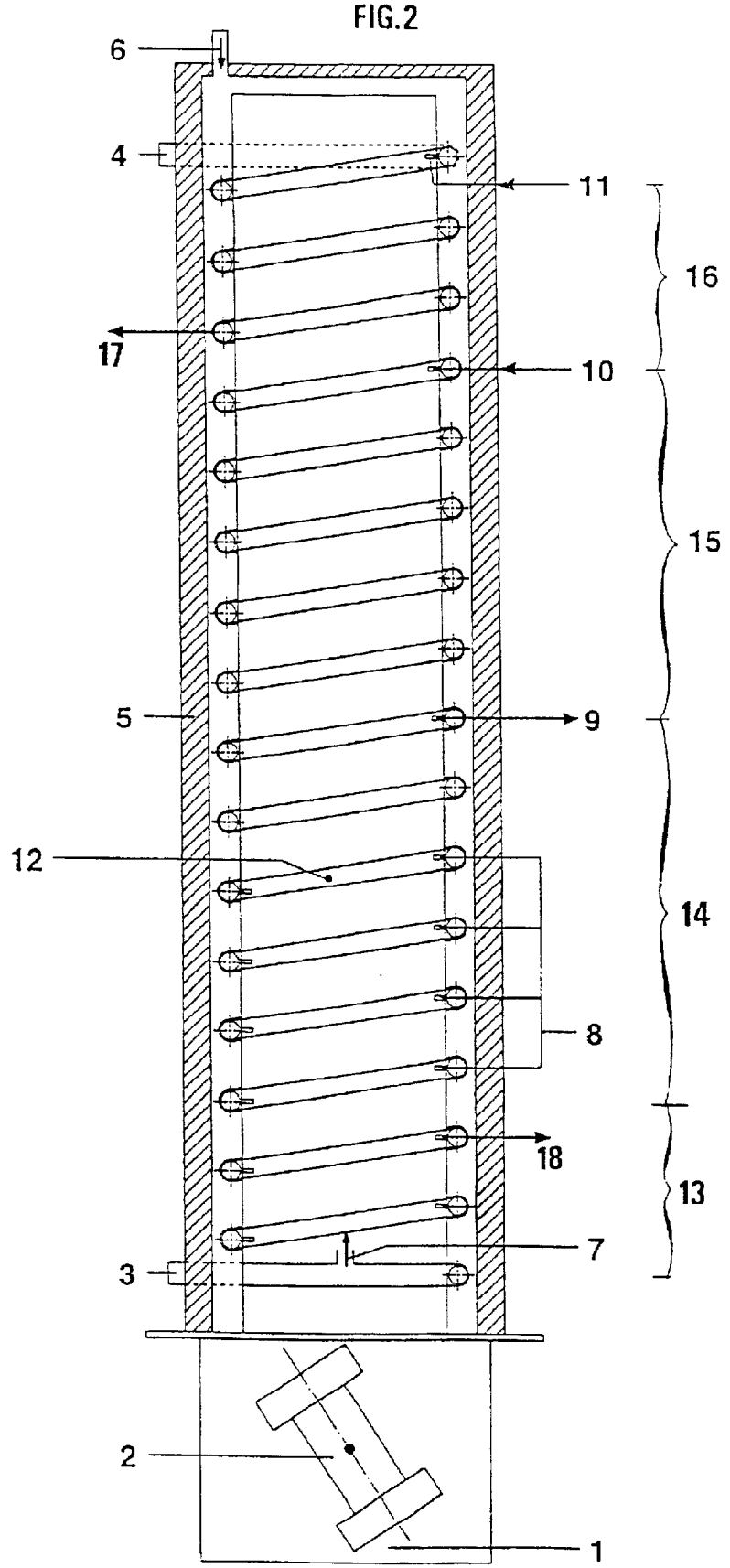

FIG. 2 describes a simple embodiment of the process according to the invention that operates in ascending mode.

Helicoidal conveyor (12) is placed on a vibrating table (1), and two unbalanced motors (2) generate the vibrations that are necessary for the catalyst to rise. The solid catalyst particles enter via hose (3) and exit via hose (4). The drum-helicoidal lifting device unit is contained in a heat-insulated container (5) that is integral with the vibrating table. An inert gas is introduced at the top of the device via hose (6). Said gas bathes the first coils (bottom) of the helicoidal lifting device: this gas is introduced into (7) laterally at the bottom of the helicoidal lifting device, and it passes through this helicoidal lifting device in co-current with the catalyst in zone (13), which is a zone for preheating and stripping hydrocarbons that are trapped in the pores of the catalyst. The inert gas that is loaded with hydrocarbons exits via hose (18). The catalyst then enters combustion zone (14), where a gas that contains air is introduced via hoses (8). The catalyst then penetrates the calcination zone (zone 15), in which it is flushed in countercurrent via a dry gas that is introduced via hose (10). The gas of the combustion and calcination zones exits from the helicoidal lifting device via hose (9). The catalyst then penetrates the cooling zone (zone 16) that is fed with dry gas in countercurrent of the catalyst via hose (11). The dry gas exits via hose (17). The feeding of hoses (8), (10) and (11) is ensured by hoses and a device that is located inside the central drum. The heating of the helicoidal lifting device is obtained by the Joule effect, by direct contact with the metal mass.

EXAMPLE 1

The catalyst of Example 1 is regenerated in a regenerator according to FIG. 2, and the lifting device that is used to produce this example comprises 17 coils, its height is 5 m and its developed length is 340 m. The catalyst comes in the form of spherical balls with a diameter of 1.8 mm, it comprises a phase that consists of rhenium heptoxide that is dispersed on alumina, and the rhenium content, expressed in metallic rhenium, is 8% by weight. The specific surface area of the catalyst is 170 m$^2$/g.

As a feedstock, the metathesis reactor uses an ethenylene+raffinate-2 steam-cracking mixture that is enriched in advance with butene-2 to produce propylene. It operates in a liquid phase at 35° C. The catalyst that is used is drawn off at the bottom of the reactor at the same time as a portion of this liquid phase. It is transferred by gravity into a chamber where the liquid phase is drained and recovered.

The catalyst then enters the regenerator at a temperature of 350° C. and at a flow rate of 500 kg/h. Its residual hydrocarbon content is 40 parts by weight per 100 parts by weight of catalyst. The first spans of the helicoidal lifting device are bathed by a nitrogen flow that is used for preheating and stripping the catalyst, zone (13). This nitrogen flow is introduced at (7) at the flow rate of 200 Nm$^3$/h, and at the pressure of 5 bar. This gas is preheated at 300° C. using a furnace that is outside of the device. It exits from zone (13) via hose (18).

The catalyst then passes through zone (14) for burning impurities, polymers, and also residual hydrocarbons that remain after the stripping in zone (13). All of hoses (8) supply a flow of 1300 Nm$^3$/h of a nitrogen-oxygen mixture at 2% by mol of oxygen, preheated to 480° C. The dwell time of the catalyst in the combustion zone (zone 14) is 1 hour, or a developed length of the helix of 120 m.

The catalyst then penetrates the calcination zone, zone (15). The catalyst is flushed there in countercurrent by a stream of air that is introduced via hose (11) that contains at most 200 ppm of water, with a flow rate of 500 Nm$^3$/h. The temperature of the injected air is such that the catalyst is brought to a temperature of 550° C. The dwell time of the catalyst in the calcination zone is 1 hour, or a developed length of the helix is 120 m.

The catalyst is finally cooled by passing through zone (16), where it is flushed in countercurrent by dry nitrogen (water content less than 50 ppm) with a flow rate of 300 Nm$^3$/h. It is transferred directly to the top of the metathesis reactor.

The device that is described in Example 1 therefore makes possible the complete regeneration of the metathesis catalyst and its transfer from the bottom of a metathesis reactor (used catalyst) to the top of the reactor (regenerated catalyst) without relying on "lifts."

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/07.984, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Installation that comprises:

at least one vibratory helicoidal conveyor (12) that comprises at least one coil, at least one hose (3) for introducing the catalyst and at least one catalyst discharge home (4), whereby this helicoidal conveyor is placed on a vibrating table (1), at least one combustion zone (14) in which is placed at least one coil of the vibratory helicoidal conveyor that comprises at least one hose (8) for introducing gases and at least one gas discharge hose (9), at least one calcination zone (15) in which is placed at least one coil of the vibratory helicoidal conveyor that comprises at least one hose (10) for introducing gases and at least one gas discharge home (9), said installation, however, does not comprise a zone in which a gas that contains a halogenated compound is introduced.

* * * * *

UNITED STATES PATENT AND TRADEMARK OFFICE
CERTIFICATE OF CORRECTION

PATENT NO.    : 6,846,465 B2
DATED         : January 25, 2005
INVENTOR(S)   : Dominique Commereuc et al.

It is certified that error appears in the above-identified patent and that said Letters Patent is hereby corrected as shown below:

<u>Column 8,</u>
Lines 28 and 37, "home" should read -- hose --.

Signed and Sealed this

Twenty-eighth Day of March, 2006

JON W. DUDAS
*Director of the United States Patent and Trademark Office*